United States Patent [19]

Schroeppel

[11] Patent Number: 5,792,203
[45] Date of Patent: Aug. 11, 1998

[54] UNIVERSAL PROGRAMMABLE CARDIAC STIMULATION DEVICE

[75] Inventor: Edward A. Schroeppel, Roswell, Ga.

[73] Assignee: Sulzer Intermedics Inc., Angleton, Tex.

[21] Appl. No.: 912,420

[22] Filed: Aug. 18, 1997

[51] Int. Cl.$^6$ .................................................. A61N 1/37
[52] U.S. Cl. ............................................................ 607/30
[58] Field of Search ................................. 607/9, 30, 59

[56] References Cited

U.S. PATENT DOCUMENTS

| 4,830,006 | 5/1989 | Haluska et al. | 128/419 |
|---|---|---|---|
| 5,403,056 | 4/1995 | Hill et al. | 607/14 |
| 5,514,161 | 5/1996 | Limousin | 607/9 |
| 5,562,708 | 10/1996 | Combs et al. | 607/4 |
| 5,584,867 | 12/1996 | Limousin et al. | 607/9 |

OTHER PUBLICATIONS

Cazeau S, Ritter P, Bakdach S, Lazarus A, Limousin M, Henao L, Mundler O, Daubert J, Mugica J: Four chamber pacing in dilated cardiomyopathy. Pace 17: 1974–79, 1994.
Bakker P, Sen K, de Jonge N, klopping C, Algra A, de Medina E, Bredee J: Biventricular Pacing Improves Functional Capacity in Patients with End–Stage Congestive Heart Failure. Pace 18: 825, 1995.
Buckingham T, Candinas R, Fromer M, Schlapfer J, Aebischer N, Jeanrenaud X, Landoit J, Kappenberger Acute hemodynamic effects of atrioventricular pacing at differing sites in the right ventricle individually and Simultaneously. Pace 18: 847,1995.
Cazeau S, Ritter P, Lazarus A, Gras D, Backdach H, Mundler O, Mugica J: Multisite pacing for end–state heart failure: early experience. Pace 19: 1748–57, 1996.

Cohen T, Mower M: Bi–ventricular pacing to improve cardiac hemodynamics. Clinical Research 38:882A 1990.

Mehra R, Hill M: Prevention of atrial fibrillation/flutter by pacing techniques. In S. Saksena et al (eds.): Interventional electrophysiology: a textbook. NY, Futura, 1996, pp. 523–524.

Primary Examiner—William E. Kamm
Attorney, Agent, or Firm—John R. Merkling; Conley, Rose & Tayon

[57] ABSTRACT

An implantable medical device, such as a pacemaker, for electrically stimulating the heart to beat includes two or more node logic units connected by communication paths over which signals between nodes are conducted. Each node can provide pacing energy to an electrode and amplify electrical signals from the electrode. In response to detecting an electrical event from the electrode or pacing an electrode, each node generates a sense signal or a pace signal. The sense and pace signals form each node can be transmitted to all other nodes with or without a time delay. The time delays between nodes are provided by delay modules controlled by a processor. As such, the implantable medical device can be configured to provide a variety of pacemaker therapies.

30 Claims, 6 Drawing Sheets

|  | TO | | | |
|---|---|---|---|---|
| FROM | RA | LA | RV | LV |
| RA | — | $P_1S$ | $P_1S$ | $P_1S$ |
| LA | $P_1S$ | — | $P_1S$ | $P_1S$ |
| RV | — | — | — | — |
| LV | — | — | — | — |

|  | TO | | | |
|---|---|---|---|---|
| FROM | RA | RV1 | RV2 | RV3 |
| RA | — | $P_1S$ | — | — |
| RV1 | — | — | $P_1S$ | — |
| RV2 | — | — | — | P |
| RV3 | — | — | — | — |

UNIVERSAL PROGRAMMABLE CARDIAC STIMULATION DEVICE

BACKGROUND OF THE INVENTION

1. Field of the Invention

The present invention relates generally to cardiac stimulating devices. More particularly, the present invention relates to a flexible and programmable cardiac stimulating device that permits a variety of cardiac therapies to be implemented.

2. Description of the Related Art

Figure 1:
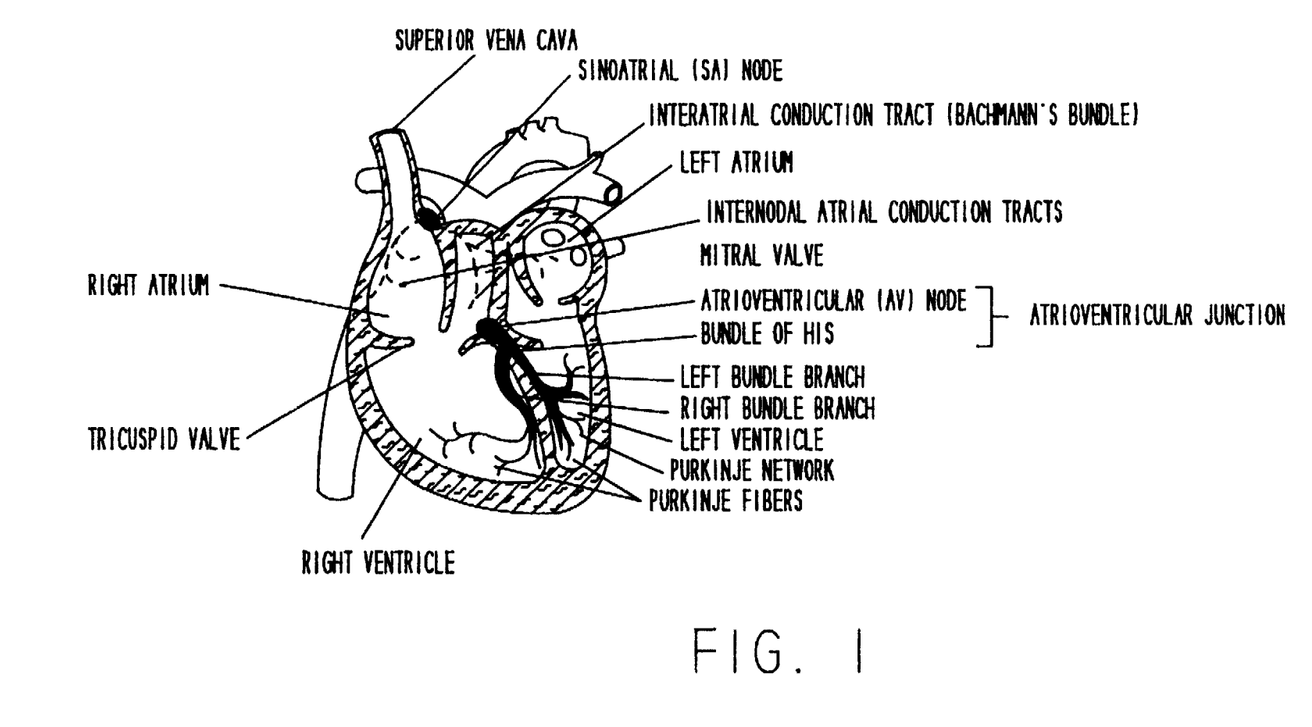
FIG. 1 is a schematic cut-away view of a human heart, in which the various relevant parts are labeled.

In the normal human heart, illustrated in FIG. 1, the sinus (or sinoatrial (SA)) node generally located near the junction of the superior vena cava and the right atrium constitutes the primary natural pacemaker by which rhythmic electrical excitation is developed. The cardiac impulse arising from the sinus node is transmitted to the two atrial chambers (or atria) at the right and left sides of the heart. In response to excitation from the SA node, the atria contract, pumping blood from those chambers into the respective ventricular chambers (or ventricles). The impulse is transmitted to the ventricles through the atrioventricular (AV) node, and via a conduction system comprising the bundle of His, or common bundle, the right and left bundle branches, and the Purkinje fibers. The transmitted impulse causes the ventricles to contract, the right ventricle pumping unoxygenated blood through the pulmonary artery to the lungs, and the left ventricle pumping oxygenated (arterial) blood through the aorta and the lesser arteries to the body. The right atrium receives the unoxygenated (venous) blood. The blood oxygenated by the lungs is carried via the pulmonary veins to the left atrium.

This action is repeated in a rhythmic cardiac cycle in which the atrial and ventricular chambers alternately contract and pump, then relax and fill. Four one-way valves, between the atrial and ventricular chambers in the right and left sides of the heart (the tricuspid valve and the mitral valve, respectively), and at the exits of the right and left ventricles (the pulmonic and aortic valves, respectively, not shown) prevent backflow of the blood as it moves through the heart and the circulatory system.

The sinus node is spontaneously rhythmic, and the cardiac rhythm it generates is termed normal sinus rhythm ("NSR") or simply sinus rhythm. This capacity to produce spontaneous cardiac impulses is called rhythmicity, or automaticity. Some other cardiac tissues possess rhythmicity and hence constitute secondary natural pacemakers, but the sinus node is the primary natural pacemaker because it spontaneously generates electrical pulses at a faster rate. The secondary pacemakers tend to be inhibited by the more rapid rate at which impulses are generated by the sinus node.

Disruption of the natural pacemaking and propagation system as a result of aging or disease is commonly treated by artificial cardiac pacing, by which rhythmic electrical discharges are applied to the heart at a desired rate from an artificial pacemaker. An artificial pacemaker (or "pacer" as it is commonly labeled) is a medical device which delivers electrical pulses to an electrode that is implanted adjacent to or in the patient's heart in order to stimulate the heart so that it will contract and beat at a desired rate. If the body's natural pacemaker performs correctly, blood is oxygenated in the lungs and efficiently pumped by the heart to the body's oxygen-demanding tissues. However, when the body's natural pacemaker malfunctions, an implantable pacemaker often is required to properly stimulate the heart. An in-depth explanation of certain cardiac physiology and pacemaker theory of operation is provided in U.S. Pat. No. 4,830,006.

Pacers today are typically designed to operate using one of three different response methodologies, namely, asynchronous (fixed rate), inhibited (stimulus generated in the absence of a specified cardiac activity), or triggered (stimulus delivered in response to a specified hemodynamic parameter). Broadly speaking, the inhibited and triggered pacemakers may be grouped as "demand" type pacemakers, in which a pacing pulse is only generated when demanded by the heart. To determine when pacing is required by the pacemaker, demand pacemakers may sense various conditions such as heart rate, physical exertion, temperature, and the like. Moreover, pacemaker implementations range from the simple fixed rate, single chamber device that provides pacing with no sensing function, to highly complex models that provide fully automatic dual chamber pacing and sensing functions. The latter type of pacemaker is the latest in a progression toward physiologic pacing, that is, the mode of artificial pacing that most closely simulates natural pacing.

Because of the large number of options available for pacer operation, an industry convention has been established whereby specific pacer configurations are identified according to a code comprising three or four letters. A fifth coded position may be used to describe a pacemaker's ability to respond to abnormally high heart rates (referred to as tachycardia). Because most pacemakers do not provide any antitachycardia functions, the fifth coded position is not used in most commonly used pacemaker types. Thus, most common configuration codes comprise either three or four letters, as shown in Table I below. For this reason and for simplicity's sake, the fifth code position is omitted from the following table. Each code can be interpreted as follows:

TABLE I

| | Code position | | | |
|---|---|---|---|---|
| | 1 | 2 | 3 | 4 |
| Function Identified | chamber paced | chamber sensed | response to sensing | programmability, rate modulation |
| Options Available | 0 - none | 0 - none | 0 - none | 0 - none |
| | A - atrium | A - atrium | T - triggered | P - programmable |
| | V - ventricle | V - ventricle | I - inhibited | M - multi- |
| | D - dual | D - dual | D - dual | programmable |
| | (A + V) | (A + V) | (T + I) | C - communicating |
| | | | | R - rate modulating |

For example, a DDD pacer paces either chamber (atrium or ventricle) and senses in either chamber. Thus, a pacer in DDD mode, may pace the ventricle in response to electrical activity sensed in the atrium. A VVI pacer paces and senses in the ventricle, but its pacing is inhibited by spontaneous electrical activation of the ventricle (i.e., the ventricle paces itself naturally). In VVIR mode, ventricular pacing is similarly inhibited upon determining that the ventricle is naturally contracting. With the VVIR mode, the pacer's pacing rate, however, in the absence of naturally occurring pacing, is modulated by the physical activity level of the patient. Pacers commonly include accelerometers to provide an indication of the patient's level of physical activity.

As illustrated in the table above, it may be desired to sense in one cardiac chamber (i.e., detect electrical activity representative of contraction of the chamber and referred to as a "sensed event") and, in response, pace (referred to as a "paced event") in the same or a different chamber. It also may be desired to pace at two electrode locations following a sensed event at one of the pacing electrodes or at a different electrode. For example, patients with abnormally fast atrial rhythms (referred to as atrial tachyarrhythmias) are often treated with pacemakers that include an electrode in each of the two atrial chambers and a third electrode in the right ventricle. Both atrial chambers usually are paced following a sensed event in either chamber. These patients often require additional pacing in the right ventricle via the ventricular electrode. A pacemaker protocol in which two or more electrode sites are paced is referred to as "multisite pacing." Multisite pacing is used to treat or prevent many types of cardiac problems such as atrial tachyarrhythmias, insufficient cardiac output and congestive heart failure. Multisite pacing normally requires at least three electrodes.

In general, many pacemaker configurations require sensing and/or pacing at one electrode following a time delay after a paced or sensed event at the same or a different electrode. For example, in one embodiment of multisite pacing, a single electrode is placed in the right atrium and three electrodes are placed in the right ventricle. The ventricular electrodes are implanted approximately in a line down the right ventricle so that pacing proceeds down the ventricle from the uppermost electrode to the bottommost electrode. Only one ventricular electrode paces at a time and a time delay controlled by the pacemaker separates one ventricular paced event from the next.

Alternatively, a patient may require ventricular pacing following a time delay after a sensed event by an atrial electrode. Further still, other patients may require a pacemaker that paces at one electrode site following a time delay after another electrode is paced. Such a delay may be necessary to prevent "crosstalk" in which a first electrode senses a paced event from a second electrode and the pacemaker confuses the paced event as a sensed event detected by the first electrode. In response to the crosstalk from the second electrode, the pacemaker inappropriately may inhibit pacing of the first electrode when otherwise pacing should not be inhibited.

The pacemaker protocols discussed above represent only a few of the many protocols required for the numerous cardiac conditions for which pacemaker therapy is indicated. Thus, modern pacemaker therapy requires the availability of many different types of pacemakers in which pacing and/or sensing may occur at any electrode following a paced and/or sensed event at any other electrode, with or without a delay. The size of the delay, if a delay is required, depends on the particular electrode placement and configuration, the pacing protocol desired, the physiology of the patient's heart, as well as other concerns.

The variety of pacemaker configurations and protocols required forces pacemaker manufacturers to design and manufacture a variety of pacemakers. Manufacturing many different types of pacemakers, however, increases the cost of manufacturing and ultimately the price paid for the pacemaker. Further, it is cumbersome for hospitals and doctors to keep track of the multitude of different models of pacemakers available from each manufacturer.

For these reasons, a pacemaker is needed with a flexible architecture that can be used to provide any configuration and protocol desired for a patient. With such a device, pacemaker manufacturers would be able to manufacture fewer different models of pacemakers, thereby reducing the cost of manufacturing and burden placed on doctors and hospitals.

SUMMARY OF THE INVENTION

Accordingly, there is herein provided an implantable and programmable medical device such as a pacemaker for electrically stimulating the heart to beat. The pacemaker architecture includes two or more node logic units connected by communication paths through which signals are communicated from one node to the next. Each node includes an output amplifier that provides pacing energy to the heart through an electrode. A pace output logic unit generates a pace output signal when the chamber of the heart in which the electrode is implanted is paced. The node also includes a sense amplifier for amplifying electrical energy from the heart via the electrode. A sense output logic unit coupled to the sense amplifier generates a sense output signal upon detection of an electrical event by the electrode. The node also includes four programmable delay modules that provide control signals to the output and sense amplifier circuits after a paced or sensed event and following a time delay.

In accordance with a preferred embodiment, each node can be configured to provide its sense and pace output signals to all other nodes without a time delay. Alternatively, a node can be configured to provide its sense and pace output signals to only a subset of the other nodes. Each node may receive as input signals pace and sense signals from any or all other nodes. The pace and sense input signals to a node are used to control the operation of that node. A node thus is controlled by its own pacing and sensing activity as well as pacing and sensing activity from one or more other nodes. The time delays between nodes are provided by delay modules controlled by a processor. The processor also programs the delay modules within each node.

Accordingly, an implantable medical device as described above can be configured to provide many, if not all, pacing therapies. The medical device can be configured during implantation and reconfigured afterwards using an external programmer.

BRIEF DESCRIPTION OF THE DRAWINGS

Other objects and advantages of the invention will become apparent upon reading the following detailed description and upon reference to the accompanying drawings, wherein.

DETAILED DESCRIPTION OF THE PREFERRED EMBODIMENT

Figure 2:
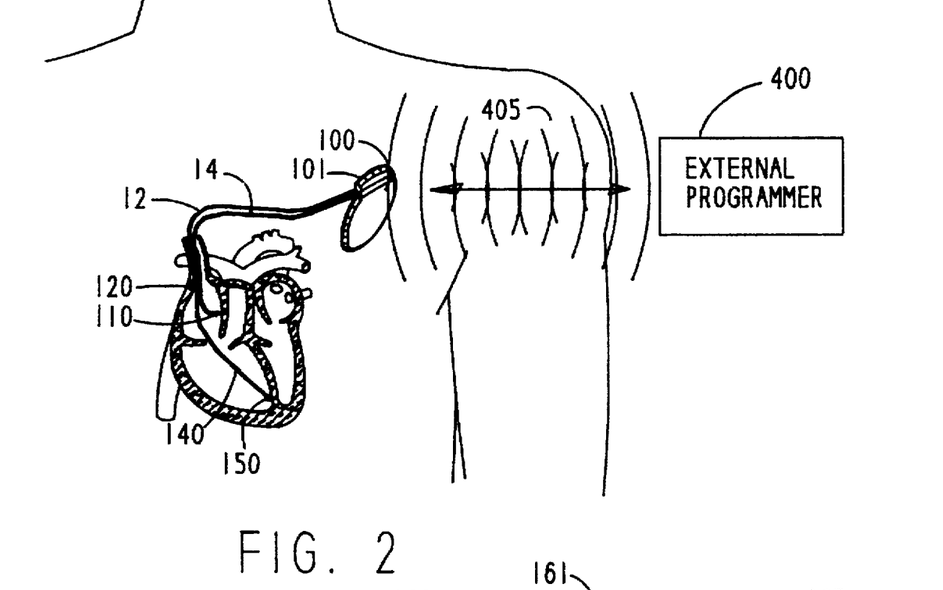
FIG. 2 is a schematic diagram of a pacemaker and external programmer constructed in accordance with the present invention and implanted in a human body.

Referring now to FIG. 2, an implantable medical device 100 constructed in accordance with the preferred embodiment is shown implanted and coupled, in an exemplary configuration, to the patient's heart by leads 12, 14. Medical device 100 also communicates with an external programmer 400, described in more detail below. The communication path between medical device 100 and external programmer 400 is indicated by reference numeral 405. The implantable medical device 100 may include a pacemaker or any medical device that performs pacing functions, including many defibrillators. For purposes of describing the preferred embodiments of the invention, however, the implantable medical device will hereafter be described as an implantable pacemaker or simply pacer 100. However, it should be understood that the invention may be employed in any of a variety of implantable medical devices, such as defibrillators.

The arrangement shown in FIG. 2 represents a dual chamber pacing configuration in which two leads 12 and 14 are coupled to a housing or "can" 101. The leads are positioned in the right ventricle and right atrium of a patient's heart, respectively. Each lead 12, 14 includes two stimulating and sensing electrodes for delivery of electrical impulses to excitable myocardial tissue in the appropriate chamber(s) in the right side of the patient's heart. More specifically, lead 14 includes a tip cathode electrode 110 and a ring anode electrode 120, and lead 12 includes a tip cathode electrode 150 and a ring anode electrode 140.

As one skilled in the art will understand, two, three, and four lead devices all have been used or suggested as various pacemaker configuration schemes and may be employed in the present invention. Thus, the configuration shown in FIG. 2 is intended to be exemplary only of the many configurations possible for a pacemaker. As will be seen below, a preferred embodiment of the invention includes a pacemaker that can be implanted with any number of leads and electrodes. Further, the electrodes may be located in any desired location within any chamber of the heart. The pacemaker in accordance with a preferred embodiment is programmable to provide any desired pacing and sensing protocol.

Figure 3:
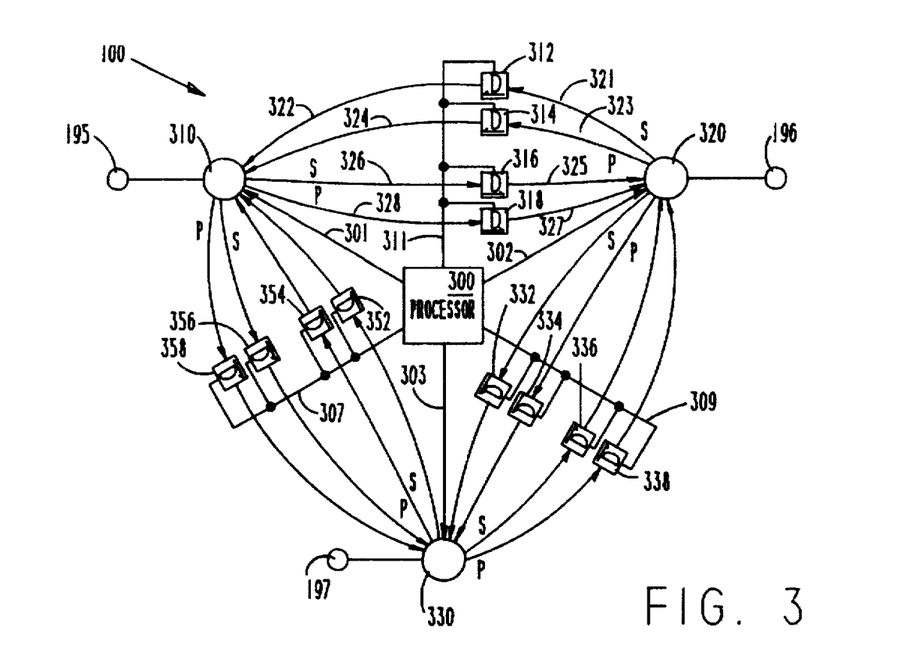
FIG. 3 is a block diagram of a pacemaker including a plurality of electrodes and logic units associated with each electrode in accordance with a preferred embodiment.

A preferred embodiment of the invention is now described with reference to the three electrode system shown in FIG. 3. Referring to FIG. 3, the pacemaker system 100 preferably includes three electrodes 195, 196, 197. In addition, the pacemaker system includes node logic units (or simply "nodes") 310, 320, and 330 coupled to electrodes 195, 196, 197. Each pair of nodes is interconnected by four communication paths; each communication path including a delay module. Each delay module delays a signal from one node to the next. Each node 310, 320, 330 preferably provides one sense output signal S and one pace output signal P to the other two nodes in the system (for sake of clarity each sense and pace output signal is shown in FIG. 3 as two output signals). The sense signal may be a digital signal that is asserted by a node upon detection of electrical activity at the electrode. The sense signal thus is asserted when the heart chamber contracts in which the electrode is implanted. The node may also provide pacing energy to the heart via the electrode. The pace output signal P is asserted by a node when the node paces the heart. The pace output signal P preferably is a digital signal that indicates when the chamber is paced.

Accordingly, node 320 provides a sense output signal on line 321 to delay module 312 and a pace output signal on line 323 to delay module 314. The delayed output signals from delay modules 312 and 314 are provided as input signals to node 310. Accordingly, the input signals to node 310 from delay modules 312 and 314 are provided on lines 322 and 324. Similarly, node 310 provides a sense output signal on line 326 to delay module 316 and a pace output signal on line 328 to delay module 318. The delayed output signals from delay modules 316, 318 are provided to node 320 via lines 325 and 327, respectively.

Sense and pace signals between nodes 310 and 330 and nodes 320 and 330 are provided in substantially the same manner for nodes 310 and 320. Accordingly, delay module 352 delays a sense output signal from node 330 to a delayed sense input signal to node 310. Delay module 354 delays a pace output signal from node 330 to a delayed pace input signal to node 310. Delay module 356 delays a sense output signal from node 310 to a delayed sense input signal at node 330, and delay module 358 delays a pace output signal from node 310 to a delayed pace input signal at node 330. Delay modules 332, 334, 336, and 338 similarly interconnect sense and pace signals between nodes 320 and 330.

The pacemaker system shown in FIG. 3 also includes a processor 300 which controls the amount of delay in each of the delay modules interconnecting the nodes 310, 320 and 330. Thus, processor 300 controls delay modules 312, 314, 316, 318 via control signals on lines 311. Processor 300 also controls delay modules 352, 354, 356, and 358 via control signals on lines 307 and delay modules 332, 334, 336, 338 via control signals on lines 309. Further, the processor controls the operation of nodes 310, 320, and 330 via lines 301, 302, and 303.

In accordance with the preferred embodiment in FIG. 3, the time delay associated with each delay module is independently controlled by processor 300 and can be programmed by external programmer 400 (FIG. 2). The architecture can easily be extended to include four or five nodes, or any other desired number of nodes. It should be recognized that as the number of nodes increases, so does the number of edges connecting the nodes. Examples of four node systems are discussed below with reference to FIGS. 10 and 12.

Figure 4:
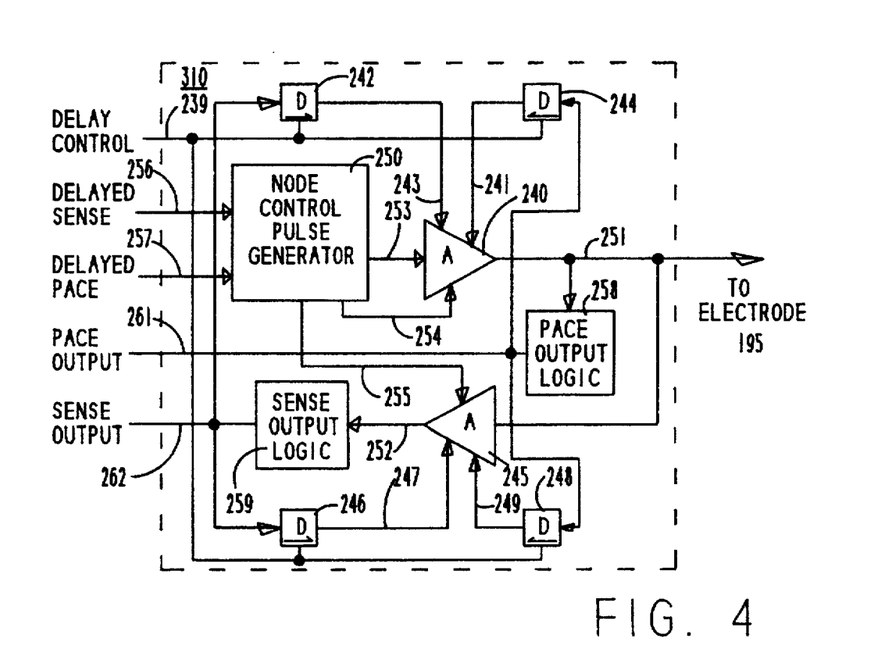
FIG. 4 is a block diagram of the logic units associated with each electrode in accordance with a preferred embodiment.

Each node 310, 320, 330 in FIG. 3 preferably includes the same logic and will be described with reference to node 310. Referring now to FIG. 4, node 310 generally includes an output amplifier 240, a sense amplifier 245, a node control and pulse generator 250, pace output logic 258, sense output logic 259, and delay modules 242, 244, 246, 248. The node circuitry preferably is implemented in an electronic assembly included within the pacemaker housing. The node control and pulse generator 250 provides a pacing signal on line 253 to output amplifier 240. The output amplifier 240 amplifies the pacing signal on line 253 and generates an appropriate output pacing signal on line 251 to electrode 195 coupled to node 310. The magnitude and time duration of the pacing signal from output amplifier 240 on line 251 is programmed into the node control and pulse generator 250 in accordance with known pacemaker protocol techniques. The sense amplifier 245 amplifies the voltage on line 251 from the electrode and provides an amplified version of the electrode signal on output line 252. The output amplifier 240 and sense amplifier 245 preferably are low power amplifiers that amplify an analog input signal and produce analog output signals. Thus, output amplifier 240 provides pacing energy to the heart via an electrode and sense amplifier 245 senses the electrical signal from the heart at the site of the electrode.

The pace output logic 258 preferably receives the analog pacing signal on line 251 from output amplifier 240 and generates a pace output signal indicative of a paced event on line 261. Similarly, the sense output logic 259 receives the analog output signal from sense amplifier 245 via line 252 and generates a sense output signal on line 262 indicative of a sensed event. The pace and sense output signals preferably include a digital value or other signal to indicate that a paced and sensed event has occurred.

In addition to delay modules between nodes (FIG. 3), each node preferably includes delay modules 242, 244, 246, and 248 to provide various delays to signals within the node. The delay time associated with each delay module is programmable in processor 300 via control lines 239. Delay module 242 provides the sense output signal from the sense output logic 259, following a time delay, to the output amplifier 240 as a control signal on line 243. Similarly, the delay module 244 provides the pace output signal from the pace output logic 258, following a time delay, as a control input signal on line 241 to the output amplifier 240. Further, following a delay, the delay module 246 provides the sense output signal from the sense output logic 259 as a control signal to the sense amplifier 245 via line 247. Finally, delay module 248 provides the pace output signal from the pace output logic 258 as a control input signal on line 249 to the sense amplifier 245. The control signals to the amplifiers 240, 245 on lines 241, 243, 247, 249 control the operation of the amplifiers. Specifically, the control signals can be asserted to inhibit the output amplifier 240 from emitting a pacing signal to the electrode and inhibit the sense amplifier 245 from sensing the voltage from the electrode. Alternatively, the control signals on lines 241, 243 can be provided to the node control and pulse generator 250, instead of the output amplifier, to inhibit the node control and pulse generator 250 from providing an input pacing signal on line 253 to the output amplifier 240. Further, the sense amplifier control signals on lines 247, 249 can be provided to the sense output logic 259, rather than the sense amplifier, to inhibit the sense output logic 259 from producing a sense output pulse on line 262.

The node logic described above advantageously allows the node's pacing function to be controlled by both paced and sensed events associated with the node. For example, the output amplifier 240 provides a pacing signal to the electrode in response either to a paced event or sensed event via control signals on lines 241 and 243, respectively. Further, delay module 244 allows the node 310 to produce a pacing signal to the electrode after a time delay following a paced event. Similarly, delay module 242 allows the node 310 to produce a pacing signal after a time delay following a sensed event. The length of delay following a paced or sensed event before a pacing signal is provided to the electrode is controlled independently for each delay module 242, 244 by a processor (FIG. 3) via control lines 239 which are represented in FIG. 3 as control lines 301, 302, and 303.

The logic of node 310 also provides for full control over the node's sensing function. Thus, the sense amplifier 245 is triggered to detect sensed events following either a paced or sensed event via delay modules 248 and 246, respectively. Sensing may be triggered upon detection of a sensed event by sense output logic 259 after a delay as determined by delay module 246. Alternatively or in addition to, sensing may also be activated upon detection of a paced event following a delay as determined by delay module 248. As for delay modules 242 and 244, the delay times associated with delay modules 246, 248 are independently controlled via signals on control lines 239.

The sense and pace output signals from all other nodes are provided as input signals via lines 257 and 256, respectively, to the node control and pulse generator 250. The node control and pulse generator preferably responds to one or more of the sense and pace input signals on lines 256, 257 by providing control signals on lines 254 and 255 to the output amplifier 240 and sense amplifier 245. These control signals, like the control signals on lines 241, 243, 247, 249, inhibit the pacing and sensing functions of the node. Rather than controlling sense amplifier 245, control signal 255 alternatively may be provided to the sense output logic as described above with respect to the control signals on lines 247, 249. Additionally, instead of providing a control signal on line 254 to the output amplifier 240, node control and pulse generator 250 instead may inhibit pacing by simply not providing an input pacing signal to the output amplifier on line 253. Thus, the universal architecture of the preferred embodiment of the invention allows the pacing and sensing activity of one node to be controlled by paced and sensed events associated with any other node in the system.

Figure 5:
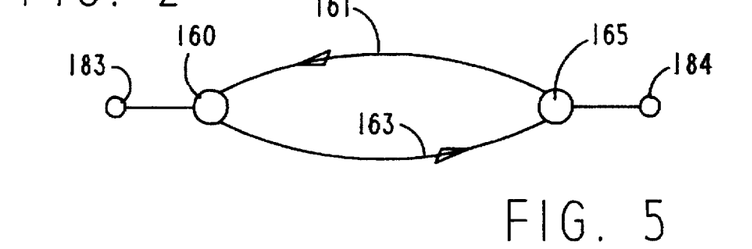
FIG. 5 is an alternative embodiment to the pacemaker of FIG. 3 with two electrodes.
Figure 6:
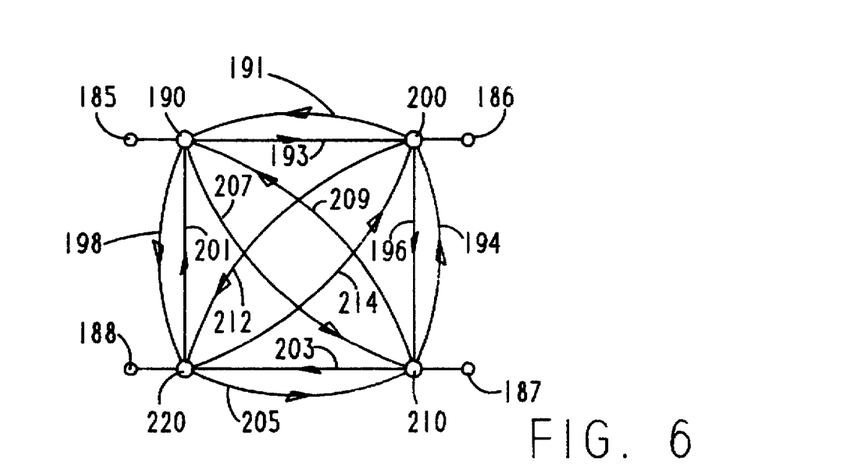
FIG. 6 is another embodiment to the pacemaker of FIG. 3 with four electrodes.

The preferred embodiment of pacemaker 100 illustrated in FIG. 3 is a three node (three electrode) system. Alternatively, pacemaker 100 can be configured with different numbers of electrodes. In FIG. 5, a two node system includes nodes 160, 165 coupled to electrodes 183,184. Each node preferably provides a pace and a sense signal to the other node by way of communication paths 161,163. Each communication path preferably includes a programmable delay module (not shown for sake of simplicity). By way of an additional example, a four node system is shown in FIG. 6 and includes nodes 190, 200, 210, 220 coupled to electrodes 185,186,187,188 respectively. Each node provides pace and sense signals to all other nodes via communication paths 191,193,194,196,198, 201,203,205,207,209, 212, and 214.

Figure 7:
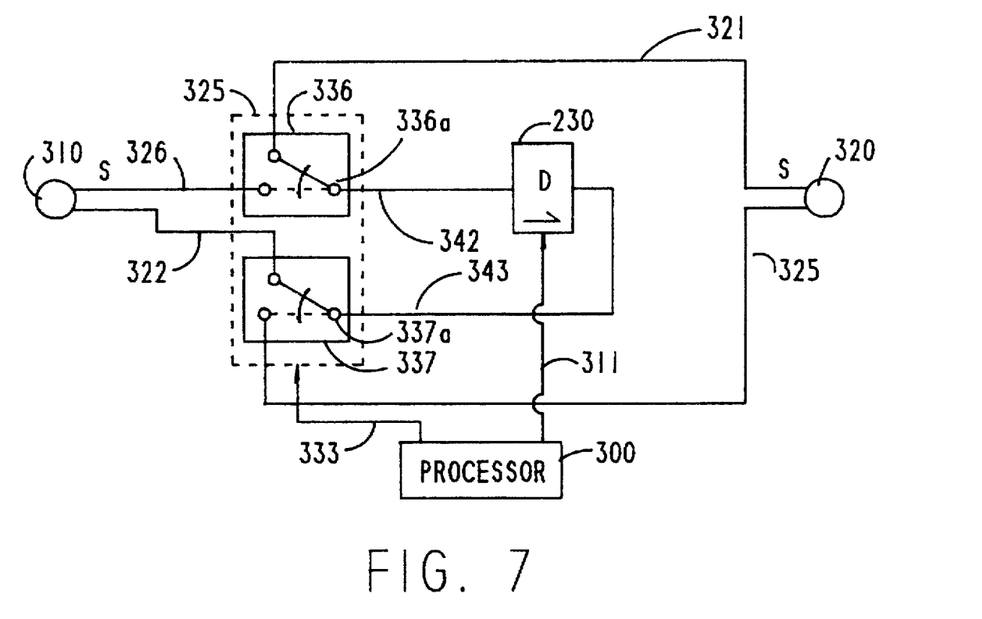
FIG. 7 shows a switching arrangement used to reverse the direction of the delay modules of FIG. 3.
Figure 8:
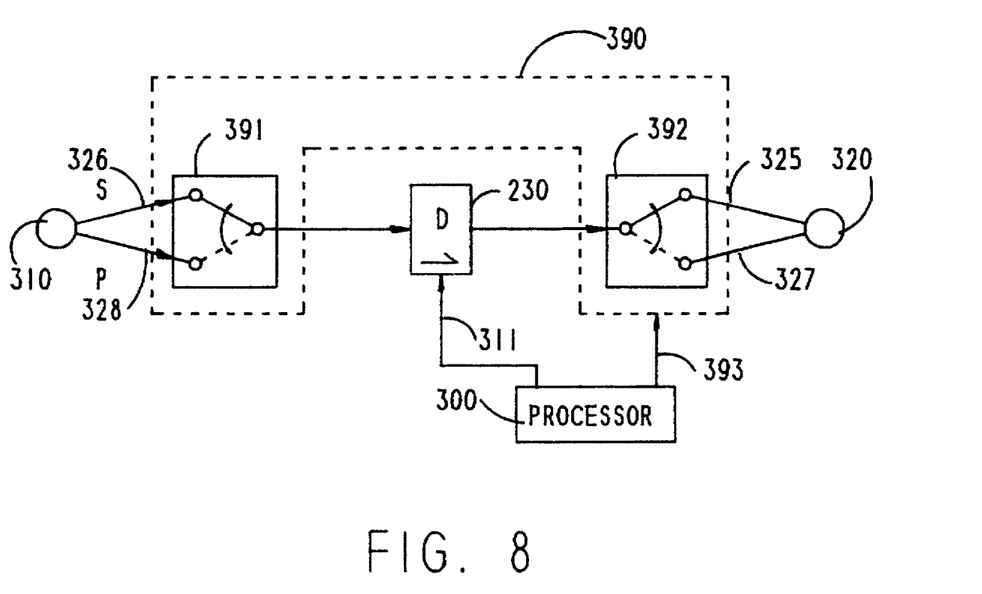
FIG. 8 shows a switching arrangement used to allow sharing of a delay module.
Figure 10:
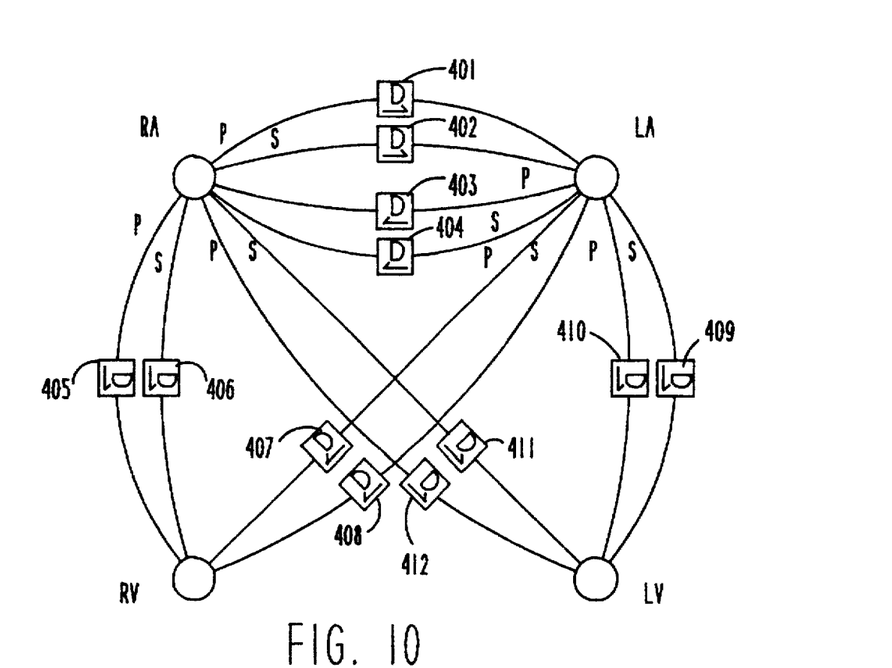
FIG. 10 depicts an exemplary four chamber, four electrode pacemaker.

The pacemaker system of FIG. 3 includes a separate delay module for each pace and sense signal provided between pairs of nodes. FIGS. 7 and 8 include alternative embodiments in which a single delay module can be used to replace two delay modules. In FIG. 7 a single delay module is used to provide a delay for signals passing in opposite directions between two nodes. In FIG. 10, a single delay is used to provide a delay for pace and sense signals provided from one node to another node in the same direction.

Referring first to FIG. 7, a single delay module 230 delays the sense output signals from each of the nodes 310 and 320. A switch 335, under control by processor 300 via control line 333, connects the delay module 230 to the nodes to delay each node's sense signal. The switch 335 preferably is configured as a double pole, double throw switch and includes two switches 336, 337 as shown. Each switch 336, 337 includes a pole 336a, 337a and two contacts. As is commonly known for a double pole, double throw switch, all switches it contains are forced to the same state. That is, the poles 336a, 337a in switches 336, 337 will couple to the comparable contacts in each switch; either in the state shown in FIG. 7 or in the alternative state indicated by the dashed lines between the poles and the lower contact shown.

With switches 336, 337 in the state shown in FIG. 7, the sense signal from node 320 on line 321 is delayed by delay module 230 and provided as a delayed sense signal on line 322 to node 310. The sense signal on line 321 conducts through switch 336, line 342, delay module 230, line 343, switch 337, and line 322 to node 310. By asserting the control signal on line 333, processor 300 can command the double pole, double throw switch 335 to the alternative state shown by the dashed lines in switches 336 and 337. Once switches 336, 337 are switched to the alternative state, the sense signal from node 310 on line 326 conducts through switch 336, line 342, delay module 230, line 343, switch 337, and line 325 to node 320.

The switching arrangement in FIG. 7 does not permit the delay module 230 to delay both sense signals simultaneously. Therefore, the arrangement of FIG. 7 may not be preferred if it is possible for both sense signals to be asserted simultaneously. Simultaneously detected sense events generally do not occur, however, because the electrodes associated with the nodes are implanted in different locations in the heart and it takes a finite amount of time for an electrical signal to propagate through the tissues of the heart from one electrode to another. Thus, two electrodes will generally not simultaneously register a sensed event resulting from a common electrical signal propagating through the heart.

Referring still to FIG. 7, to provide added flexibility the processor can program the delay module 230, via control line 311, to provide different time delays for each of the sense signals. Moreover, the switch and delay module configuration in FIG. 7 can be used to delay any pair of signals transmitted in opposite directions between nodes and independently control the amount of delay associated with each signal.

Referring now to FIG. 8, a single delay module can also be used to delay pace and sense signals conducted in the same direction between a pair of nodes. Switch 390 preferably includes a double pole, double throw switch, and accordingly includes switches 391 and 392. Like switches 336, 337 in FIG. 7, switches 391, 392 are controlled in tandem by a control signal on line 393 from processor 300. With switches 391, 392 in the state shown in FIG. 8, the sense signal from node 310 on line 326 is provided to node 320 via switch 391, delay module 230, switch 392 and line 325. Via the control signal on line 393 to switches 391, 392, processor 300 can command switches 391, 392 to the alternative state shown by the dashed-lines in the switches. Once in the alternative state, the pace signal from node 328 is provided to node 320 via switch 391, delay module 230, switch 392, and line 325. Further, processor 300 can program delay module 230 to have a different delay for the sense signal on line 326 as compared to the delay desired for the pace signal on line 328. Additionally, it should be recognized that additional switches can be added to allow a single delay module to be shared by more than two signals.

Figure 9:
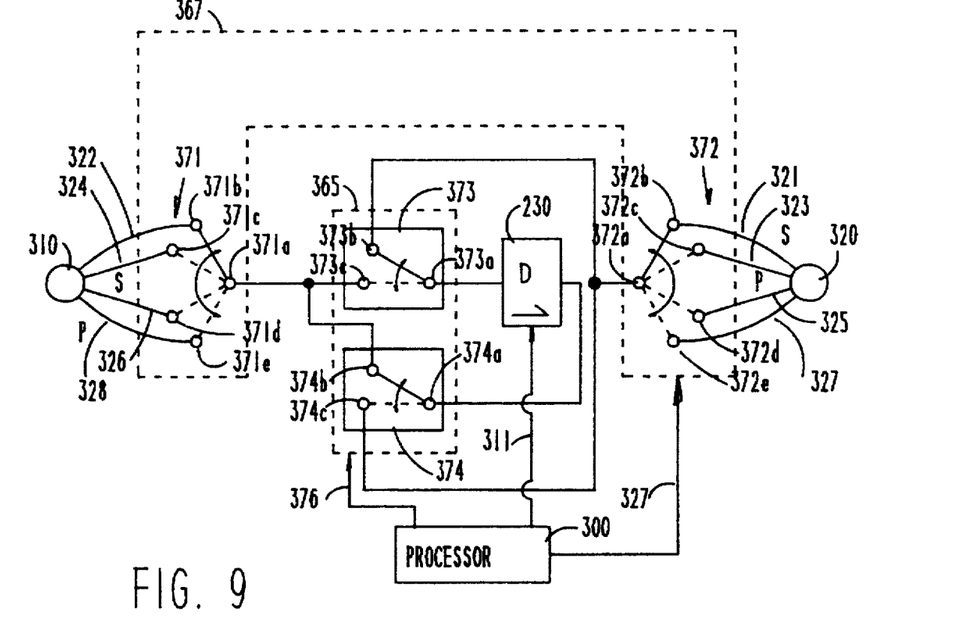
FIG. 9 shows a switching arrangement used both to reverse the direction of a delay module and to provide sharing of a delay module.

The embodiment shown in FIG. 7 allows delay reversal for signals conducting between nodes in opposite directions. The embodiment of FIG. 8 allows a single delay module to be shared between nodes for at least two signals passing in the same direction between nodes. Referring now to FIG. 9, both delay module reversal and delay module sharing are shown using switches 365, 367 to pace and sense signals between nodes 310 and 320. Switch 365 includes switches 373 and 374 and allows delay module 230 to be reversed, similar to switch 335 in FIG. 7, thereby delaying pace and sense signals in either direction between nodes 310 and 320. The state of switch 365 is determined by a control signal on line 311 from processor 300. Switch 367 is a two pole, four throw switch including switches 371 and 372 which are controlled in tandem by a control signal on line 377 from processor 300. Processor 300 independently controls switches 365, 367 by asserting control signals on lines 311, 376. As shown in FIG. 9, delay module 230 with switches 365, 367 can be used to replace the four delay modules 312, 314, 316, 318 between nodes 310 and 320 of FIG. 3.

With the state of switches 367, 365 as shown in FIG. 9 (i.e., pole 371b connected to contact 371a, pole 372b connected to contact 372a, and poles 373a, 374a connected to contacts 373b and 374b, respectively), the sense signal from node 320 on line 321 is provided to node 310. The conducting path for the sense signal from node 320 includes line 321, switch 372, switch 373, delay module 230, switch 374, switch 371 and line 322. The pace signal from node 320 conducts along a similar path once switches 371 and 372 are switched to the state in which the poles 371a and 372a connect to contacts 371c and 372c.

The sense and pace signals from node 310 are provided to node 320 in a reverse direction by changing the state of switches 373 and 374 to the alternate state in which poles 373a and 374a connect to contacts 373c and 374c. The sense signal from node 310 conducts along a path including switch 371 (with its pole 371a connected to contact 371d), switch 365, delay module 230, switch 374, switch 372, and line 325. The pace signal from node 310 follows a similar path after processor 300 directs switches 371 and 372 to change states so that poles 371a and 372a connect to contacts 371e and 372e, respectively. Additionally, processor 300 preferably programs delay module 230 to provide the desired delay for each sense and pace signal.

Thus, the many individual delays represented by the edges and nodes of the multi-site pacemaker, in accordance with the preferred embodiment, may be reduced to fewer delay modules, as desired. The switches in FIGS. 7–9 preferably include electronic switches constructed of low power CMOS or other integrated circuit technologies. Although depicted as discrete elements in FIGS. 3–4, 7–9, the delay modules may alternatively be implemented in software by the processor 300, as would be known by those of ordinary skill in the art.

The description of the preferred embodiment discussed above represents a universal architecture for implantable medical devices such as pacemakers. The time delay associated with all of the delay modules shown in FIGS. 3–4, 7–9 preferably are programmable via control signal inputs from processor 300. Further, any time delay may be programmed to a value of 0 (i.e., no delay) or to any other value.

The pacemaker configuration of FIG. 3 is completely connected in that all pairs of nodes are connected by communication paths. It may be desired, however, to configure a pacemaker system that is not completely connected (i.e., some pairs of node are not connected by communication paths). Thus, the pacemaker 100 preferably can be configured to either provide a delay path between a pair of nodes, or not, as desired. Being able to configure the pacemaker's communication paths in any manner desired allows the pacemaker to provide a wide variety of pacemaker therapies, when previously multiple pacemakers were required to provide the desired therapies. One technique for indicating no connection is to be made between a particular pair of nodes is to program the delay module(s) associated with the pair of nodes to a value that is defined to mean no connection is desired. For example, a delay time of 100 seconds may be used to indicate that no connection is needed.

Thus, given a set of implanted electrodes coupled to a pacemaker, any configuration such as those shown and discussed above is possible. The configuration desired can be programmed during implantation of the pacemaker or programmed in a post surgical follow-up visit using the external programmer 400 shown in FIG. 2. In accordance with the preferred embodiment, the external programmer 400 receives configuration data from the implanted pacemaker reflecting the particular configuration in which the pacemaker currently is operating. Programmer 400 may download a new configuration data set to the pacemaker to program the pacemaker to a new configuration. Many techniques are possible for encoding the configuration of the pacemaker, a few of which are discussed below with reference to FIGS. 10–13.

Referring now to FIG. 10, a four node system includes nodes for the right atrial electrode (RA), right ventricular electrode (RV), left atrial electrode (LA), and left ventricular electrode (LV). The configuration shown in FIG. 10 corresponds to a four-chamber pacemaker with one electrode in each of the chambers of the heart. Referring still to FIG. 10, the RA node provides pace and sense signals via delay modules 401, 402, 405, 406, 411, and 412 to the LA, RV, and LV nodes. Similarly, the LA node provides pace and sense signals via delay modules 403, 404, 407, 408, 409, and 410 to the RA, RV, and LV nodes.

Figure 11:
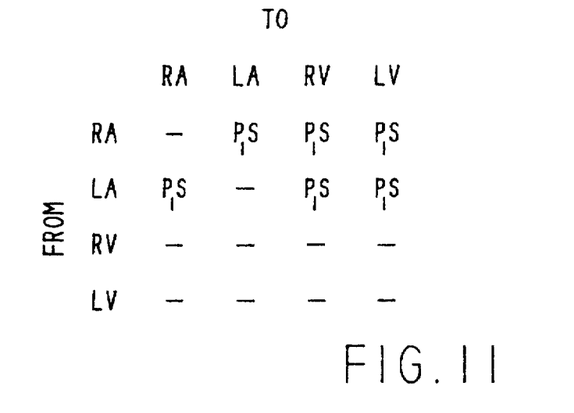
FIG. 11 is the tabular representation of the pacemaker of FIG. 10.

Referring to FIG. 11, the configuration of FIG. 10 is shown in tabular form in which "P" signifies that a connection provides a pace output signal to be transmitted between the nodes indicated and "S" signifies that a connection provides a sense output signal between the nodes. The blanks in the table of FIG. 11 indicate that there is no connection between the associated pair of nodes. As such, the table of FIG. 11 reflects the linear graph configuration for the pacemaker system of FIG. 10. It should be recognized that additional information may be necessary to fully configure a pacemaker. Such additional information generally includes the time delay values associated with each delay module, the sense amplifier sensitivity, pulse amplitudes and widths of the output pulses to the electrodes, the bandwidth of the sense amplifiers, and other variables not reflected in the table of FIG. 11 but which can be provided to programmer 400 via known techniques.

Figure 12:
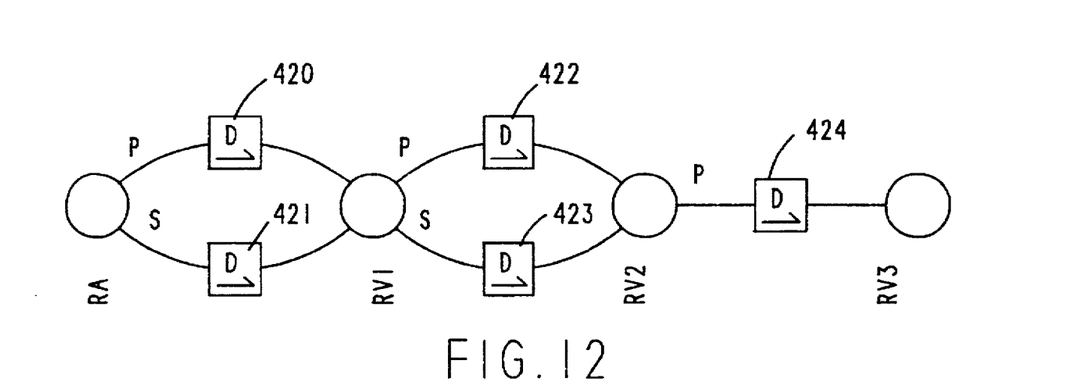
FIG. 12 depicts an exemplary four node, linear graph model with delay modules of a two chamber electrode configuration.
Figure 13:
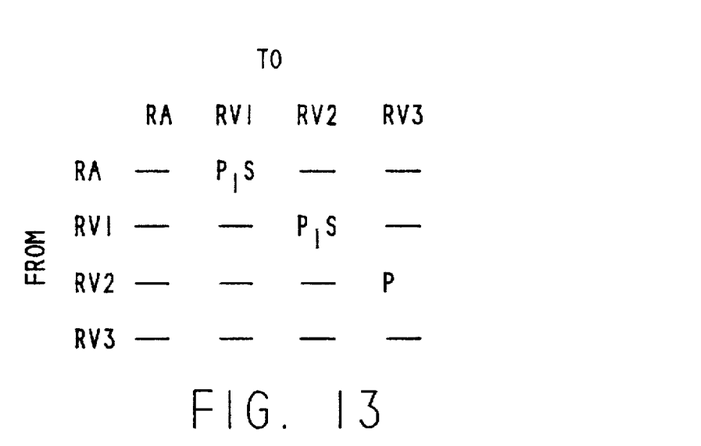
FIG. 13 shows the tabular representation of the exemplary model of FIG. 12.

By way of an additional example, FIG. 12 represents a four node pacemaker system and FIG. 13 includes the associated configuration table in accordance with the technique described above with respect to the configuration table of FIG. 11. Referring to FIG. 12, the configuration shown includes one electrode in the right atrium (represented as the RA node) and three more electrodes in the right ventricle and represented as nodes RV1, RV2, and RV3. The configuration of FIG. 12 represents a two-chamber, four-site pacemaker, such as may be implemented in a pacemaker DDD mode of operation. The RA mode provides pace and sense output signals via delay modules 420 and 421 to the RV1 node which, in turn, provides pace and sense output signals via delay modules 422 and 423 to the RV2 node. The RV2 node provides only a pace output signal to the RV3 node via a delay module 424.

Once the external programmer 400 receives the configuration of the implanted pacemaker, a new configuration may be established for the implanted pacemaker. Accordingly, the implanted pacemaker can be reconfigured by downloading a new configuration table from the programmer to the implanted device (provided the electrodes are in the desired locations). Further, the external programmer may display the configuration information.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. An implantable medical device that includes a plurality of electrodes coupled to the heart, output and sense amplifiers coupled to the electrodes, said medical device comprising:

a plurality of nodes;

a plurality of communication paths coupling said nodes, wherein a node provides output signals to any other node via said communication paths.

2. The implantable medical device as in claim 1 wherein each node includes:

pace output logic coupled to said output amplifier, said pace output logic receives an output signal from said output amplifier and generates a pace output signal upon detection of a pace event;

sense output logic coupled to said sense amplifier, said sense output logic receives an output signal from said sense amplifier and generates a sense output signal upon detection of a sense event;

node control and pulse generator coupled to said output and sense amplifiers, said node control and pulse generator provides control signals to said output and sense amplifiers; and a plurality of intra-node delay modules.

3. The implantable medical device as in claim 2 wherein said node output signals from a node are provided as input signals to said node control and pulse generator of any other node.

4. The implantable medical device as in claim 3 wherein each communication path between a pair of nodes includes an inter-node delay module that receives an output signal from one node in said pair of nodes and provides an inter-node delay module output signal representing said node output signal with a time delay to the other node in said pair.

5. The implantable medical device as in claim 4 wherein the time delay of each delay module is programmable.

6. The implantable medical device as in claim 5 wherein said node output signals include a pace output signal and a sense output signal.

7. The implantable medical device as in claim 6 wherein said intra-node delay modules include a first intra-node delay module coupled to said sense output logic and said output amplifier, said first intra-node delay module provides the sense output signal from said sense output logic following a first time delay as a first control signal to said output amplifier.

8. The implantable medical device as in claim 7 wherein said intra-node delay modules further include a second intra-node delay module coupled to said pace output logic and said output amplifier, said second intra-node delay module provides the pace output signal from said pace output logic following a second time delay as a second control signal to said output amplifier.

9. The implantable medical device as in claim 8 wherein said intra-node delay modules further include a third intra-node delay module coupled to said sense output logic and said sense amplifier, said third intra-node delay module provides the sense output signal from said sense output logic following a third time delay as a third control signal to said sense amplifier.

10. The implantable medical device as in claim 9 wherein said intra-node delay modules further include a fourth intra-node delay module coupled to said pace output logic and said sense amplifier, said fourth intra-node delay module provides the pace output signal from pace output logic following a fourth time delay as a fourth control signal to said sense amplifier.

11. The implantable medical device as in claim 10 wherein the time delays of said first, second, third, and fourth intra-node delay modules are programmable.

12. The implantable medical device as in claim 11 wherein the time delays of said intra-node and inter-node delay modules are programmable to time delays of zero seconds.

13. The implantable medical device as in claim 4 wherein said communication paths couple all pairs of nodes in said implantable medical device and each of said nodes provides an output signal to all other nodes via said communication paths.

14. A method for operating an implantable medical device that includes a plurality of electrodes and logic units associated with each electrode, said logic units generating pace and sense signals pertaining to each electrode, comprising:

providing pace and sense signals from a logic unit associated with one electrode in said plurality of electrodes to a logic unit associated with any another electrode; and controlling pacing and sensing activity of each electrode based on the pace and sense signals provided from a logic unit associated with any another electrode.

15. The method of claim 14 further including programming said implantable medical device to control pacing and sensing activity of each electrode.

16. The method of claim 15 wherein said step of providing pace and sense signals includes delaying said pace and sense signals.

17. The method of claim 16 wherein said step of programming said implantable medical device includes programming the amount of delay for delaying said pace and sense signals.

18. The method of claim 17 wherein said step of providing said pace and sense signals between logic units includes providing said pace and sense signals between every pair of logic units in said implantable medical device.

19. The method of claim 17 wherein said step of programming said implantable medical device includes defining between which pairs of logic units said pace and sense signals are to be provided.

20. The method of claim 19 wherein said step of controlling the pacing and sensing activity of each electrode is further based on said pace and sense signals from the logic unit associated with the electrode being controlled.

21. A medical system for electrically stimulating the heart, comprising:

a programmable medical device;

a plurality of leads coupled to said implantable medical device;

a plurality of electrodes disposed on said leads;

wherein said programmable implantable medical device includes a plurality of nodes associated with said electrodes, said medical device is programmable to provide communication paths between any pair of nodes, said communication paths used to provide pace and sense signals from one node to another node.

22. The medical system of claim 21 wherein each node includes pace output logic that generates a pace output signal upon detection of a paced event and sense output logic that generates a sense output signal upon detection of a sensed event.

23. The medical system of claim 22 wherein said communication paths include programmable inter-node delay modules that time delay said pace and sense output signals between nodes.

24. The medical system of claim 23 further including an external programmer that programs said inter-node delay modules.

25. The medical system of claim 24 wherein said external programmer also determines which pairs of nodes includes communication paths.

26. The medical system of claim 25 wherein each node includes four programmable intra-node delay modules.

27. The medical system of claim 26 wherein said external programmer also programs the time delays of the intra-node delay modules.

28. The medical system of claim 27 wherein a node control and pulse generator, an output amplifier and a sense amplifier are associated with each node and provide pacing and sensing for said node, said node control and pulse generator controls the pacing and sensing of the node in response to signals from said inter node delay modules and said intra-node delay modules.

29. The medical system of claim 24 wherein said external programmer receives the interconnection pattern of nodes and communication paths via telemetry from the programmable medical device.

30. The medical system of claim 29 wherein said external programmer displays said interconnection pattern.

* * * * *